United States Patent
Green

(10) Patent No.: US 6,908,363 B2
(45) Date of Patent: Jun. 21, 2005

(54) METHOD FOR TARGET POLISHING INTRAOCULAR LENSES

(75) Inventor: George F. Green, Victor, NY (US)

(73) Assignee: Bausch & Lomb Incorporated, Rochester, NY (US)

(*) Notice: Subject to any disclaimer, the term of this patent is extended or adjusted under 35 U.S.C. 154(b) by 114 days.

(21) Appl. No.: 10/184,552

(22) Filed: Jun. 27, 2002

(65) Prior Publication Data

US 2004/0002290 A1 Jan. 1, 2004

(51) Int. Cl.$^7$ .............................................. B24B 13/00
(52) U.S. Cl. ............................................... 451/29; 451/42
(58) Field of Search .................................. 451/84, 29, 30, 451/31, 38, 39, 42, 43, 57, 82

(56) References Cited

U.S. PATENT DOCUMENTS

| 1,679,369 A | * | 8/1928 | Motz ............................ 451/84 |
| 2,299,405 A | * | 10/1942 | Prange .......................... 451/75 |
| 4,555,872 A |   | 12/1985 | Yie ............................... 51/439 |
| 4,893,440 A | * | 1/1990 | Gallant et al. ................. 451/99 |
| 5,133,159 A | * | 7/1992 | Nelson .......................... 451/36 |
| 5,429,838 A | * | 7/1995 | Mansson et al. .............. 427/2.24 |
| 5,709,587 A | * | 1/1998 | Shaffer .......................... 451/38 |
| 6,264,693 B1 |  | 7/2001 | Ross ............................. 623/6.17 |

FOREIGN PATENT DOCUMENTS

| JP | 2002127015 | 5/2002 | ............. B24C/3/32 |
| WO | 01/17726 A1 | 3/2001 | ............. B24C/3/04 |
| WO | 02/16077 A2 | 2/2002 | ............. B24B/31/10 |

OTHER PUBLICATIONS

U.S. Appl. No. 10/022,101 Entitled "Polishing Mask for Intraocular Lens", filed Dec. 17, 2001 by R. Wrue.

U.S. Appl. No. 10/184,167 Entitled "Apparatus and Method for Target Polishing Intraocular Lenses", filed Jun. 27, 2002 by G. Green.

* cited by examiner

*Primary Examiner*—Robert A. Rose
(74) *Attorney, Agent, or Firm*—Craig E. Larson

(57) ABSTRACT

A method for polishing targeted areas of an IOL while leaving other areas unpolished such as sharp posterior edges designed to inhibit PCO. In the preferred embodiment, the polishing method utilizes a stream of polishing agent directed at the IOL which is mounted to a holder during the polishing operation. In this manner, only the targeted areas of the IOL polished while the other areas remain unpolished and sharp as intended. The method is suitable for in-line automated IOL manufacturing.

13 Claims, 5 Drawing Sheets

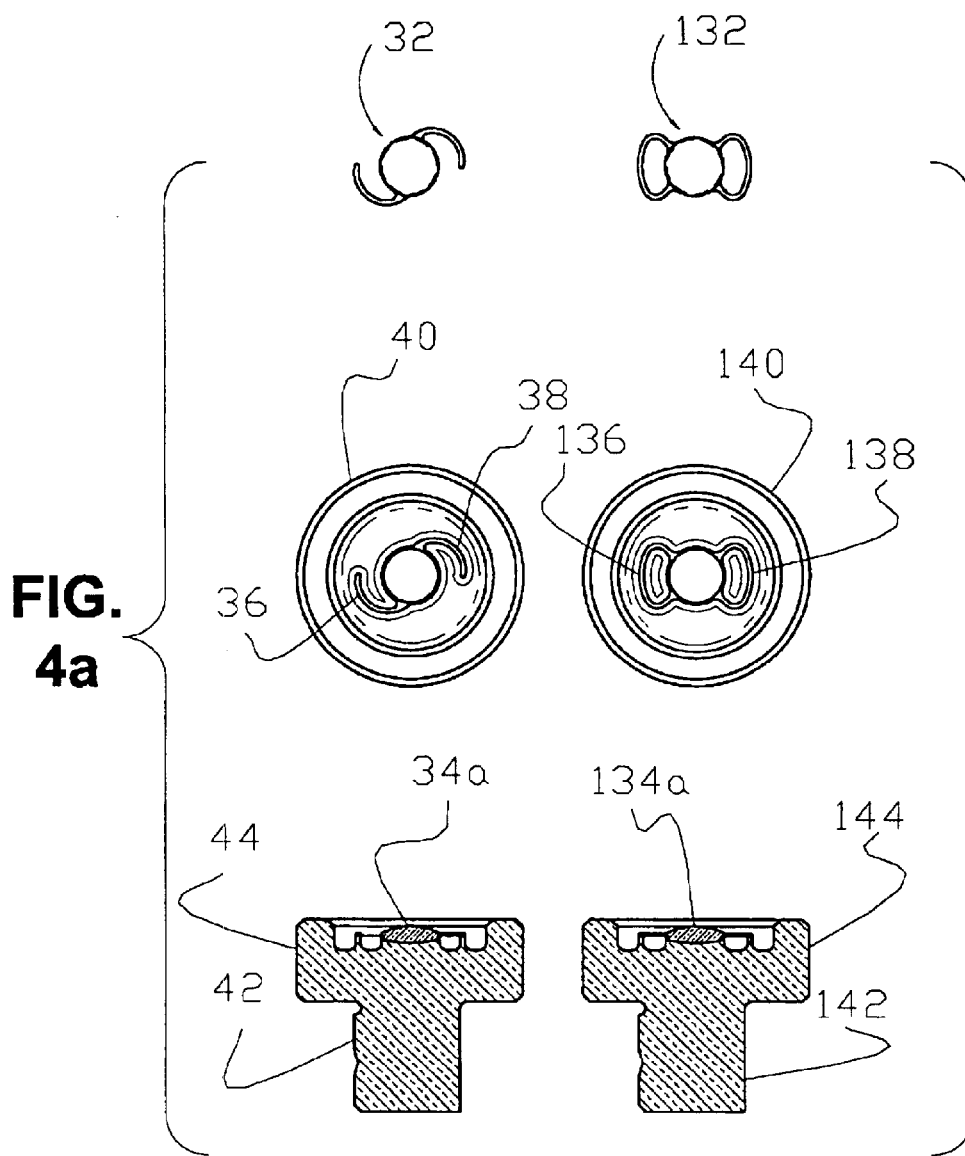
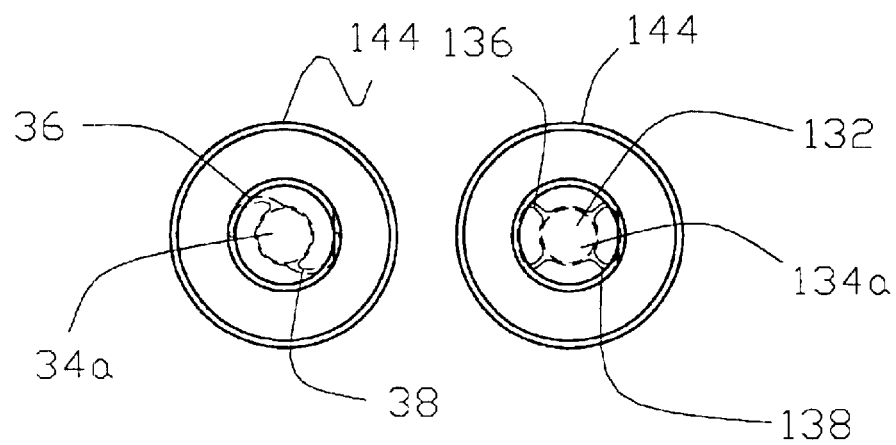
FIG. 4b   FIG. 5B

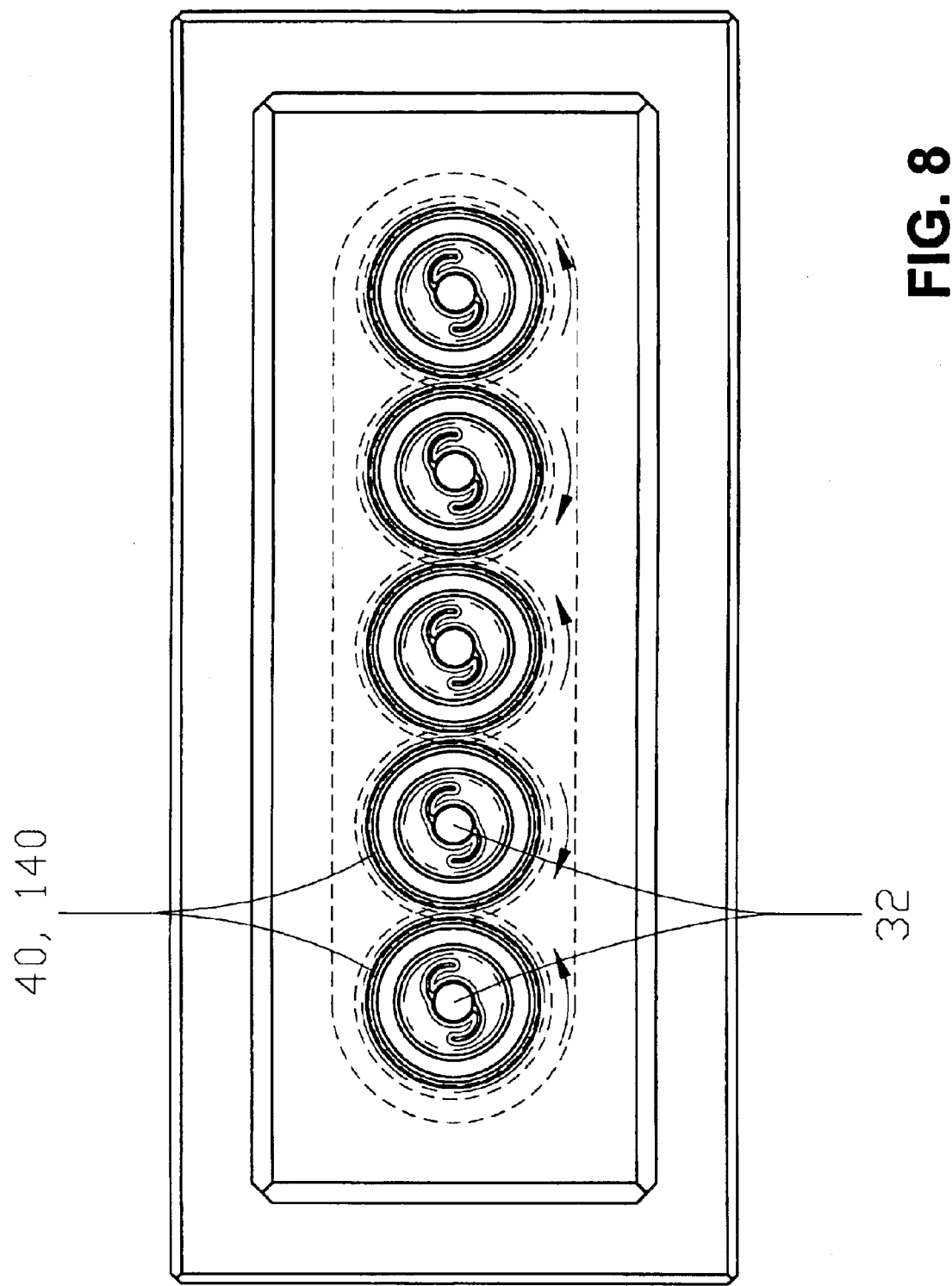

METHOD FOR TARGET POLISHING INTRAOCULAR LENSES

BACKGROUND OF THE INVENTION

The present invention relates to the manufacture of intraocular lenses (IOLs) for implantation in an eye. The present invention more particularly relates to a method for polishing selected areas of an IOL while other areas of the IOL remain unpolished.

A common and desirable method of treating a cataract eye is to remove the clouded, natural lens and replace it with an artificial IOL in a surgical procedure known as cataract extraction. In the extracapsular extraction method, the natural lens is removed from the capsular bag while leaving the posterior part of the capsular bag (and preferably at least part of the anterior part of the capsular bag) in place within the eye. In this instance, the capsular bag remains anchored to the eye's ciliary body through the zonular fibers. In an alternate procedure known as intracapsular extraction, both the lens and capsular bag are removed in their entirety by severing the zonular fibers and replaced with an IOL which must be anchored within the eye absent the capsular bag. The intracapsular extraction method is considered less attractive as compared to the extracapsular extraction method since in the extracapsular method, the capsular bag remains attached to the eye's ciliary body and thus provides a natural centering and locating means for the IOL within the eye. The capsular bag also continues its function of providing a natural barrier between the aqueous humor at the front of the eye and the vitreous humor at the rear of the eye.

One known problem with extracapsular cataract extraction is posterior capsule opacification, or secondary cataract, where proliferation and migration of lens epithelial cells occur along the posterior capsule behind the IOL posterior surface which creates an opacification of the capsule along the optical axis. This requires subsequent surgery, such as an Er:YAG laser capsulotomy, to open the posterior capsule and thereby clear the optical axis. Undesirable complications may follow the capsulotomy. For example, since the posterior capsule provides a natural barrier between the back of the eye vitreous humor and front of the eye aqueous humor, removal of the posterior capsule allows the vitreous humor to migrate into the aqueous humor which can result in serious, sight-threatening complications. It is therefore highly desirable to prevent posterior capsule opacification in the first place and thereby obviate the need for a subsequent posterior capsulotomy.

IOLs are typically either molded or lathe cut. Subsequent to either of these operations, the IOLs usually have flash, irregular, and/or roughened surfaces that need to be smoothed. It is thus usually necessary to polish the IOL to remove any flash and smooth out any rough areas on the IOL. A common IOL polishing method is tumble polishing wherein a batch of IOLs are placed in a tumbler for many hours with a polishing agent. Examples of tumble polishing IOLs may be seen in the following patents:

U.S. Pat. No. 5,133,159 discloses a method of tumble polishing silicone articles in a receptacle charged with a mixture of non-abrasive polishing beads and a solvent which is agitated to remove surface irregularities from the articles.

U.S. Pat. No. 5,571,558 discloses a tumbling process for removing flash from a molded IOL by applying a layer of aluminum oxide on a plurality of beads, placing the coated beads, alcohol, water and silicone IOLs in a container and tumbling the same to remove flash.

U.S. Pat. No. 5,725,811 discloses a process for removing flash from molded IOLs including tumbling the IOLs in a tumbling media of 0.5 mm diameter glass beads and 1.0 mm diameter glass beads, alcohol and water.

In recent years, IOLs have been purposely designed with sharp posterior edges which has been found to inhibit the migration of lens epithelial cells (LECs) between the IOL and posterior capsular bag, also known as posterior capsule opacification or "PCO" to those skilled in the art. One such method for creating a sharp posterior edge in an IOL is described in copending application Ser. No. 10/005,864 filed on Nov. 8, 2001 and of common ownership with the present application, the entire disclosure of which is incorporated herein by reference. Creating a sharp, discontinuous bend in the posterior capsule wall is widely recognized by those skilled in the art as an effective method for minimizing PCO. See, for example, *Posterior Capsule Opacification* by Nishi, *Journal of Cataract & Refractive Surgery*, Vol. 25, January 1999. This discontinuous bend in the posterior capsule wall can be created using an IOL having a posterior edge which forms a sharp edge with the peripheral wall of the IOL.

Thus, while polishing is a necessary step in the IOL manufacturing process to remove surface irregularities, a purposely formed, sharp, posterior edge is one area of the IOL which should not be polished. If this area of the IOL is not protected from the polishing operation, the sharp posterior edge will become rounded and not function to inhibit PCO as intended. There thus remains a need for a method for polishing only targeted areas of IOLs, especially IOLs having purposely formed sharp edges.

SUMMARY OF THE INVENTION

The present invention addresses the problem of polishing only targeted areas of an IOL during the polishing operation by providing a method of polishing the IOL which comprises the steps of providing and directing a controlled stream of a polishing agent at targeted areas of the IOL while the remaining areas of the IOL are substantially untouched by the polishing agent. In one particular embodiment, the method comprises the steps of a) providing an IOL to be polished;
b) fixturing the IOL on a holder with targeted areas of the IOL being exposed; and
c) providing and directing a stream of polishing agent at the exposed areas of the IOL while the remaining areas of the IOL are not polished by the polishing agent.

In a preferred embodiment of the invention, a plurality of holders are provided each having an IOL mounted thereto for polishing. In an advantageous embodiment of the invention, a plurality of IOL holders with IOLs thereon are placed in an array which may be set upon a conveyor for passing beneath one or more nozzles which direct the polishing agent in a stream at the targeted areas of the IOL. In this manner, a plurality of IOLs may be polished at a time in an automated assembly line to increase efficiencies of manufacturing.

From the above, it will be appreciated that the present method of polishing IOLs is an improvement over the prior art method of tumble polishing in that the inventive polishing operation may be targeted to just the selected areas of the IOLs while the remaining areas of the IOL remain unpolished so as to retain their original geometry. This is especially important in IOL designs having sharp edges which need to be retained sharp, e.g., to inhibit secondary cataract as explained above.

In yet a further embodiment, other selected areas of the IOL which are meant to remain unpolished may be masked to prevent the polishing agent from reaching that area of the IOL.

Various polishing agents and means may be used to polish the targeted areas of the IOL. These include polishing agents which may be directed in a controlled stream as discussed above, some examples of which include the polishing media disclosed in the prior art tumble polishing patents discussed above. Other polishing means include those used in the spectacle lens and contact lens industries; for example, an oscillating and/or rotating pad of polishing material against which the lens is engaged for polishing.

BRIEF DESCRIPTION OF THE DRAWINGS

FIG. 4a are plan and a side elevational view of the IOL of FIGS. 2 and 3 and an IOL holder on which the IOL is mounted;

FIG. 4b is a plan view of the IOL mounted to the IOL holder of FIG. 4a and ready for polishing;

FIG. 5a is a plan view and a side elevational view of an IOL having a closed-loop configuration and an IOL holder on which the IOL is mounted;

FIG. 5b is a plan view of the IOL mounted to the IOL holder of FIG. 5a and ready for polishing;

FIG. 8 is a top plan view of the array of FIG. 7.

DETAILED DESCRIPTION

Figure 1:
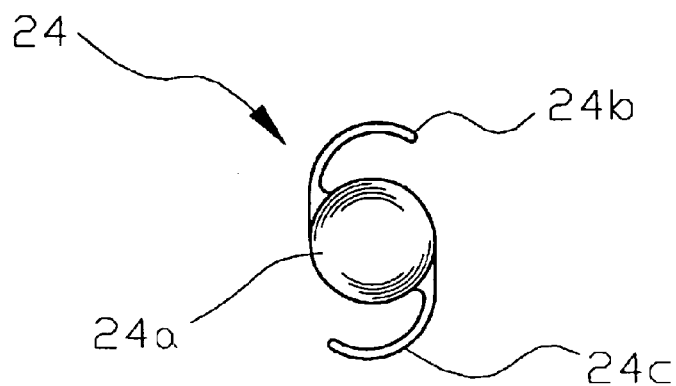
FIG. 1 is a plan view of a prior art IOL.

A prior art IOL 24 having no sharp posterior edge is seen in FIG. 1 to include an optic 24a with two haptics 24b and 24c extending therefrom in a curved fashion. Since this prior art IOL has no sharp posterior edge, it may undergo a prior art method of tumble polishing which will polish all the surfaces thereof.

Figure 2:
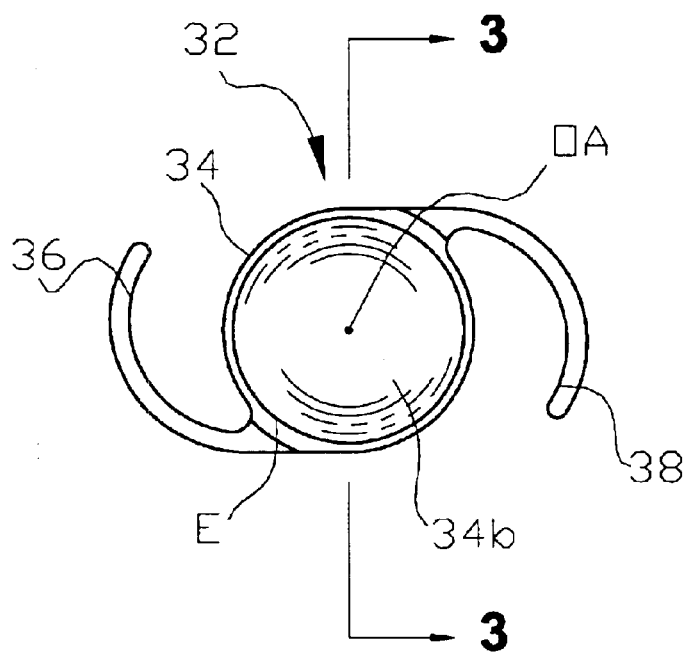
FIG. 2 is a plan view of an IOL made with a sharp posterior edge.
Figure 3:
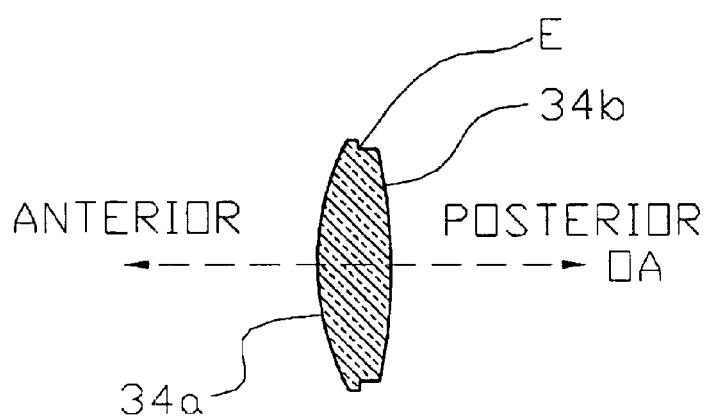
FIG. 3 is a cross-sectional view of the IOL as taken generally along the line 3—3 of FIG. 2.

FIGS. 2 and 3 show an IOL 32 having a sharp posterior edge E. Although the configuration of IOL 32 is the subject of our copending application Ser. No. 10/005,864 referred to above, it is understood that the present invention is suitable for use with any IOL requiring polishing of only targeted areas thereof (e.g., specific areas of the optic and/or haptics). IOL 32 is seen to include a central optic portion 34 having opposite anterior and posterior surfaces 34a and 34b, respectively. When implanted within the eye, anterior optic surface 34a faces the cornea 18 and posterior optic surface 34b faces the retina 20. A pair of haptics 36,38 are attached to and extend from opposite sides of the periphery of optic portion 34 and are configured to provide a biasing force against the interior of the capsule 16 to properly position IOL 32 therein. More particularly, the haptics 36,38 are configured such that upon implanting the IOL with the capsular bag, the haptics engage the interior surface of the capsular bag. The engagement between the haptics and capsule creates a biasing force causing the IOL optic 34 to vault posteriorly toward the retina 20 whereupon the posterior surface 34b of the IOL optic presses tightly against the interior of the posterior capsule wall 16a of capsule 16. It is noted that other known IOL positioning means and IOL configurations are possible. Furthermore, IOL 32 may be made from any suitable IOL material, e.g., PMMA, silicone, hydrogels and composites or combinations thereof The IOL 32 may also be a one piece or multiple piece design (e.g. where the haptics are attached to the optic after the optic is formed.)

Referring still to FIGS. 2 and 3, it is seen that IOL optic 34 has a periphery including a sharp edge E defined at the juncture of posterior surface 34b and the peripheral wall. With the haptics 36,38 providing the biasing force explained above, the optic posterior surface 34b presses tightly against the posterior capsule wall of the eye (not shown). Since the eye's capsule is somewhat resilient in nature, the force of the IOL optic against the capsule wall results in the IOL indenting into the posterior capsule wall. The sharp edge E of the IOL optic thus forcibly indents into the capsule wall and thereby creates a discontinuous bend in the posterior capsule wall at this point. As explained above, this discontinuous bend in the posterior capsule wall acts to inhibit LEC migration past this point (i.e., between the posterior capsule wall and IOL posterior surface 34b) and PCO is inhibited. It is thus critical that IOL sharp edge E remain sharp throughout the manufacturing operations including the polishing operation.

Referring now to FIGS. 4a,b and 5a,b a holder 40 and 140 for removably fixturing an IOL 32, 132 thereon is provided, respectively. It is noted that the IOL 32 of FIGS. 4a,b is of the open-loop type and the IOL 132 of FIGS. 5a,b is of the closed-loop type to show but two different configurations of IOL which may be polished using the present inventive polishing apparatus and method. Other configurations of IOL are possible and within the scope of the invention and the IOLs of FIGS. 4a,b and 5a,b are simply used for ease of description. Similar parts are denoted by similar numerals in FIGS. 4a,b and 5a,b with the numerals in FIGS. 5a,b being increased by 100 to distinguish the parts from those of FIGS. 4a,b.

Holder 40, 140 may be of any desired configuration so long as it performs the function of holding IOL 32, 132 during the polishing operation. In the embodiment shown in the drawing, holder 40, 140 includes a stem 42, 142 and head portion 44, 144 on which IOL is positioned for the polishing operation. Examples of materials which could be used to removably mount IOL 32 to head portion 44 include wax, pitch, adhesive and the like. A vacuum head may also be used to hold the IOL in place during polishing. It is noted that many IOLs are produced by lathing and milling. In the lathing operation, the IOL is a button which is held in a lathe chuck for lathing of the posterior surface. The IOL is then turned over and mounted to a holder with the IOL posterior surface facing down on the holder. The anterior surface of the optic is then lathed and the IOL profile, including the haptics, is milled. After this step in the prior art method, the IOL is removed from the holder and placed into a tumble polisher for polishing. Conversely, in the present inventive method, the IOL remains attached to the holder for polishing, although it is understood that the IOLs may be formed in any desired manner (e.g., cast or compression molded) while still utilizing and realizing the benefits of the present invention. It is furthermore noted that it is preferred that the IOL is in a dry state (i.e., not hydrated) while undergoing the polishing operation of the present invention.

Thus, the IOL 32, 132 is readied for the polishing operation by being mounted onto the holder 40, 140 with the IOL anterior surface 34a, 134a facing upward and the posterior surface 34b in facing contact with the block. In this position, anterior surface 34a is facing upwardly and it, along with the respective haptics thereof, are exposed while posterior surface 34b, including sharp edge E, are covered by virtue of their facing engagement with the holder.

Figure 6:
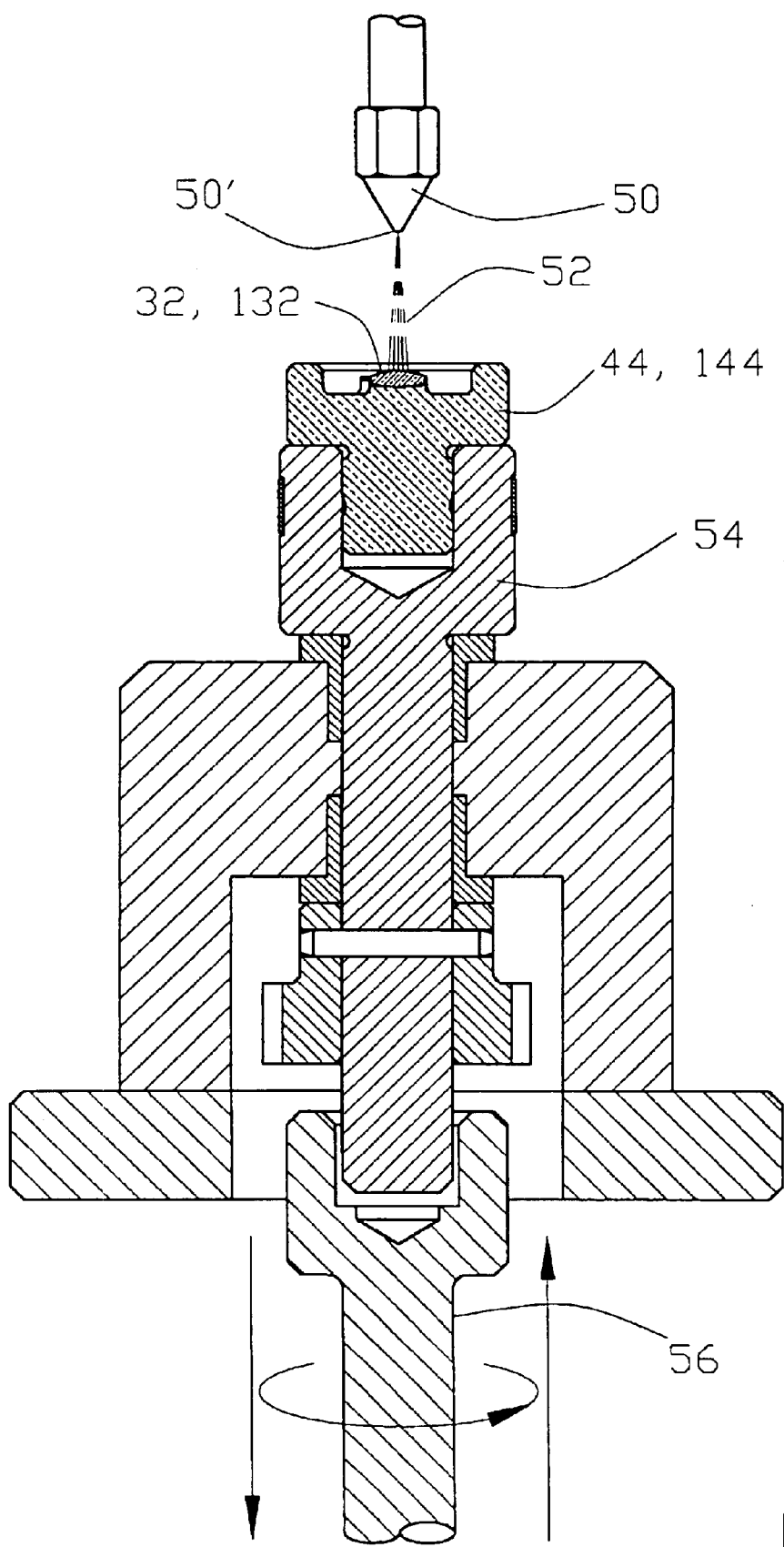
FIG. 6 is a cross-sectional, side elevational view of a holding fixture into which a respective IOL and IOL holder may be removably positioned.
Figure 7:
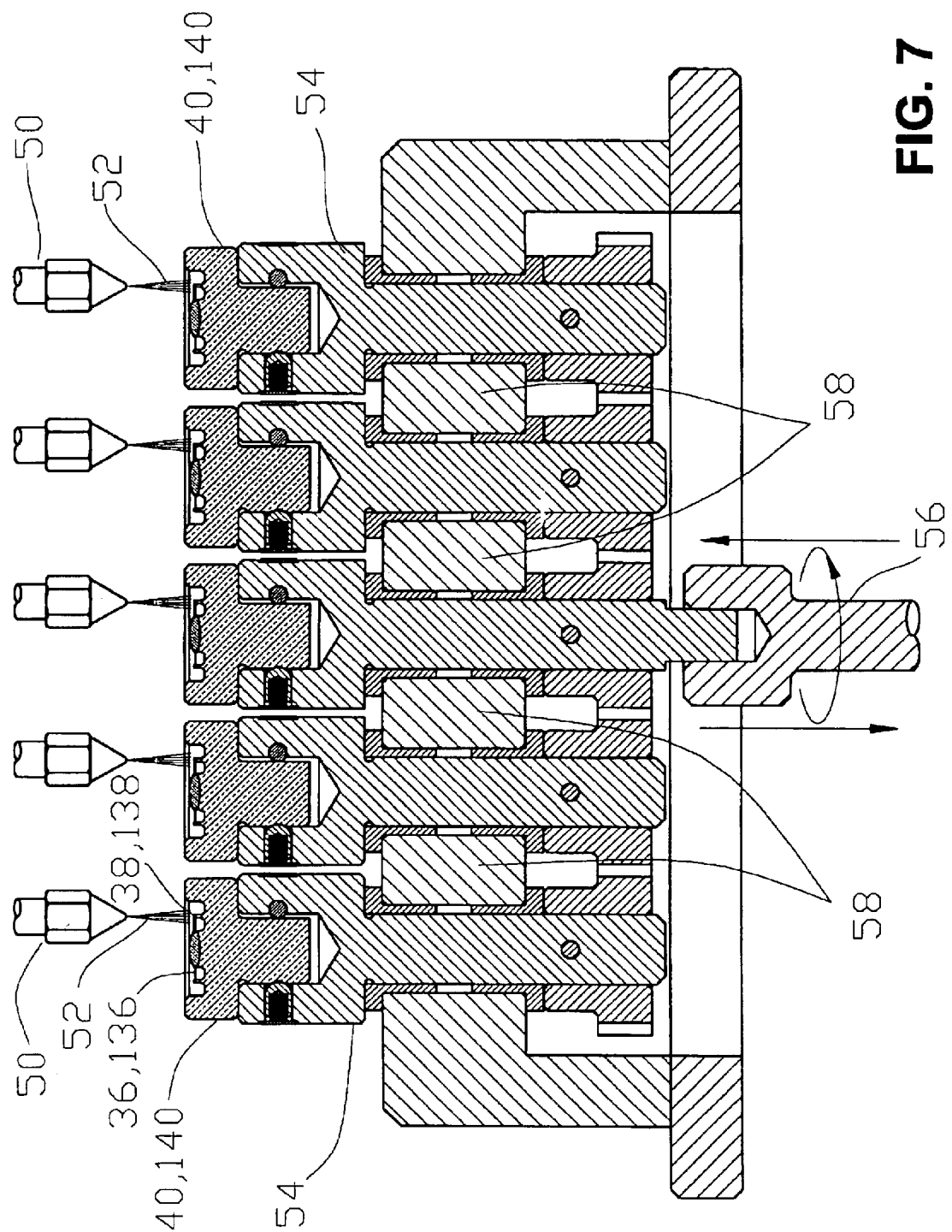
FIG. 7 is a view of a plurality of the holding fixtures of FIG. 6 positioned in an array with the polishing nozzles directed at the IOLs mounted on the holders.

Referring now to FIGS. 6–8, a preferred embodiment of the polishing operation of the invention will now be described. In the preferred embodiment, a polishing agent is provided and delivered under pressure through a nozzle 50 in a polishing stream 52 and directed at targeted areas of IOL 32, 132 while mounted on holder 44,144. As stated above, the polishing agent may be any known polishing agent such as those used in prior art tumble polishing (e.g., a glass bead, alcohol and water slurry). The stream profile 52 may be regulated via the nozzle exit orifice 50' which has continuous adjustability between a wide stream profile or a very narrow stream profile. The viscosity of the polishing agent may also be adjusted until the desired stream flow and profile is achieved.

It is noted that depending on the stream profile and the configuration of the IOL being polished, it may be necessary to move the polishing stream relative to the IOL being polished during the polishing operation. In this instance, either the holder and IOL may be moved while the nozzle 50 remains stationary or the IOL holder and IOL may remain stationary while the nozzle is moved relative thereto. Alternatively, both the IOL holder and IOL and the nozzle may be moved at the same time. One method for rotating the IOL holder is illustrated in FIGS. 6–8 which show the IOL holder 40,140 removably secured in a chuck 54 which may be set rotating by drive shaft 56 coupled thereto. A plurality of such rotating chucks 54 may be placed in an array such as shown in FIGS. 7 and 8 to increase efficiencies of manufacturing. A single drive shaft 56 may be used to rotate a linearly extending array of chucked IOL holders as illustrated via gearing 58 although other known arrangements for moving the holders may of course be employed.

In operation, the array of blocked IOLs are positioned beneath one or more nozzles 50 which are directed at the targeted portions of the IOL. As stated above, it may be desirable to move the nozzle 50 relative to the respective IOL holder and IOL being polished. In this regard, the nozzle may be mounted upon a robotic arm (not shown) for precisely controlled movement along the targeted areas of the IOL. For example, in FIG. 7, it is seen that each nozzle 50 is directing the stream of polishing agent 52 along just the haptic portion of the IOL, respectively. Once the haptics are polished, the nozzle may be directed at the exposed anterior surface of the optic portion for polishing that targeted part of the IOL.

It will be appreciated that those areas of the IOL that are not impinged by the polishing stream 52 are left unpolished. This includes any exposed areas purposely not impinged by the polishing stream, as well as those areas covered by virtue of covered engagement with the IOL holder 40, 140. This would include the posterior optic surface 34b along with the sharp peripheral edge E thereof. As stated previously, masking (not shown) may also be employed to cover those areas of the IOL which should not be polished. The masking would be applied to those portions of the IOL that are not to be polished and as such, those areas of the IOL would be protected from the polishing spray. Examples of IOL masking methods may be seen in our commonly owned, copending patent application Ser. No. 10/022,101 filed on Dec. 17, 2001 and Ser. No. 10/184,167 filed on even date herein, both of which are incorporated herein in their entirety by reference.

The present inventive apparatus and method of IOL polishing is much more efficient than prior art IOL polishing methods such as tumble polishing in that only the targeted surfaces of the IOL are polished, and the time to polish the IOL is much quicker than in tumble polishing (e.g., on the order of minutes for the inventive method versus upwards of 72 hours or more for tumble polishing). Once the IOLs have been polished according to the invention hereof, the IOLs may be subject to further processing as required (e.g., vacuum coating, hydration, sterilization, etc.).

What is claimed is:

1. A method of polishing targeted areas of an IOL having one or more sharp edges wherein the sharp edges are unpolished and remain sharp through the polishing operation, said method comprising the steps of:
   a) placing said IOLs on a holder with said targeted areas exposed;
   b) covering said sharp edges from said polishing operation; and
   c) providing a polishing agent directed in a stream at said targeted areas of said IOL and thereby polishing said targeted areas of said IOL while said sharp edges remain unpolished and sharp.

2. The method of claim 1 wherein said polishing agent is directed through a nozzle having an adjustable exit orifice.

3. The method of claim 1 wherein a plurality of said holders with respective lOLs thereon are positioned in an array.

4. The method a of claim 3 wherein a respective plurality of nozzles are positioned for directing a respective stream of polishing agent at said respective plurality of IOLs.

5. The method of claim 4 wherein said nozzles are moved relative to said respective IOLs through a robotic arm during said polishing operation.

6. The method of claim 4 wherein said IOLs are rotated relative to said respective nozzles during said polishing operation.

7. The method of claim 4 wherein said IOLs and said respective nozzles are both moved relative to each other during said polishing operation.

8. The method of claim 1 wherein said IOL includes one or more haptics, and wherein said targeted areas of said IOL include said one or more haptics.

9. The method of claim 1 therein said IOL includes one or more haptics, and wherein said targeted areas of said IOL include said one or more haptics.

10. The method of claim 1 wherein said IOL includes an optic having opposite anterior and posterior surfaces, and wherein said targeted areas of said IOL include said anterior surface of said optic.

11. The method of claim 1 wherein said IOL includes an optic having opposite anterior and posterior surfaces, and wherein said targeted areas of said IOL include said anterior surface of said optic.

12. The method of claim 10 wherein said IOL includes one or more haptics, and wherein said targeted areas of said IOL include said one or more haptics.

13. The method of claim 11 wherein said IOL includes one or more haptics, and wherein said targeted areas of said IOL include said one or more haptics.

* * * * *